(12) United States Patent
Liu et al.

(10) Patent No.: US 11,241,150 B2
(45) Date of Patent: Feb. 8, 2022

(54) FLEXIBLE DIGITAL URETEROSCOPE

(71) Applicant: NINGBO Wise OptoMech Technology Corporation, Ningbo (CN)

(72) Inventors: Geping Liu, San Jose, CA (US); Xibo Wei, Ningbo (CN); Xiyi Wei, Ningbo (CN)

(73) Assignee: OTU Medical Inc., a California Corporation, Union City, CA (US)

(*) Notice: Subject to any disclaimer, the term of this patent is extended or adjusted under 35 U.S.C. 154(b) by 0 days.

(21) Appl. No.: 15/649,485

(22) Filed: Jul. 13, 2017

(65) Prior Publication Data

US 2018/0140177 A1    May 24, 2018

(30) Foreign Application Priority Data

Nov. 24, 2016  (CN) .......................... 201611041752.8
Nov. 24, 2016  (CN) .......................... 201611041782.9

(51) Int. Cl.
*A61B 1/307*    (2006.01)
*A61B 1/00*    (2006.01)
(Continued)

(52) U.S. Cl.
CPC ............ *A61B 1/307* (2013.01); *A61B 1/0008* (2013.01); *A61B 1/0011* (2013.01);
(Continued)

(58) Field of Classification Search
CPC .............. A61B 1/00032; A61B 1/0008; A61B 1/00103; A61B 1/00105; A61B 1/0011;
(Continued)

(56) References Cited

U.S. PATENT DOCUMENTS

| | | | |
|---|---|---|---|
| 2009/0149948 A1* | 6/2009 | Atanasoska | A61L 29/02 623/1.42 |
| 2010/0331883 A1* | 12/2010 | Schmitz | A61B 10/0275 606/249 |
| 2017/0059848 A1* | 3/2017 | Haraguchi | G02B 23/243 |

* cited by examiner

*Primary Examiner* — Timothy J Neal
*Assistant Examiner* — William B Chou
(74) *Attorney, Agent, or Firm* — WorldPatent.Agency / 5Suns; Chein-Hwa Tsao; YuanHui Huanq

(57) ABSTRACT

The present invention discloses a flexible digital ureteroscope that is at least partially disposable. The ureteroscope comprises a single-use catheter and a handle. The catheter comprises a distal end, a bend portion, and a proximal portion. The distal end has a rigid or semi-rigid shell that houses a set of micro lenses, an image sensor microchip, and a plurality of LED light sources. A working channel extends along the entire catheter and is coupled to a working channel port on the handle to receive various medical devices and irrigation lines during an endoscopic procedure. In addition, the catheter includes one or more steering wires to control the distal end to bend towards a desired direction. The rigid or semi-rigid shell of the distal end is made of a mix of polymer composite material with graphene nano-filler for enhancing thermal dissipation. The handle may be a single-use handle or a reusable handle. In case the handle is a reusable handle, it includes a battery module and a wireless communication module for communicating with a host machine wirelessly. In case the handle is a single-use handle, to reduce cost, the handle does not include a battery module and/or a wireless communication module. Rather, the single-use handle includes a host interface for receiving power from the host machine and transmits image data to the host machine.

11 Claims, 14 Drawing Sheets

(51) Int. Cl.
- A61B 1/05 (2006.01)
- H04N 5/225 (2006.01)
- H04N 5/374 (2011.01)
- A61B 1/06 (2006.01)
- A61B 1/12 (2006.01)
- A61B 1/005 (2006.01)
- A61B 1/018 (2006.01)
- A61L 29/12 (2006.01)
- A61B 1/07 (2006.01)
- A61B 1/015 (2006.01)

(52) U.S. Cl.
CPC ........ *A61B 1/00032* (2013.01); *A61B 1/0052* (2013.01); *A61B 1/0057* (2013.01); *A61B 1/00103* (2013.01); *A61B 1/00105* (2013.01); *A61B 1/015* (2013.01); *A61B 1/018* (2013.01); *A61B 1/051* (2013.01); *A61B 1/0676* (2013.01); *A61B 1/0684* (2013.01); *A61B 1/07* (2013.01); *A61B 1/128* (2013.01); *A61L 29/126* (2013.01); *H04N 5/2252* (2013.01); *H04N 5/2256* (2013.01); *H04N 5/2257* (2013.01); *H04N 5/374* (2013.01); *A61B 1/00114* (2013.01); *A61L 2400/12* (2013.01); *H04N 2005/2255* (2013.01)

(58) Field of Classification Search
CPC ..... A61B 1/0052; A61B 1/0057; A61B 1/015; A61B 1/018; A61B 1/051; A61B 1/0676; A61B 1/0684; A61B 1/07; A61B 1/128; A61L 29/126; H04N 5/2252; H04N 5/2256; H04N 5/2257; H04N 5/374
USPC ....... 600/105, 109, 128, 129, 135, 139, 140, 600/153, 160, 175, 176, 177, 178, 179
See application file for complete search history.

FLEXIBLE DIGITAL URETEROSCOPE

CROSS-REFERENCE TO RELATED APPLICATIONS

This application claims priority to Chinese Patent Application No. 201611041752.8 filed on Nov. 24, 2016 and Chinese Patent Application No. 201611041782.9 filed on Nov. 24, 2016, the entire contents of which are incorporated by reference herein.

FIELD OF INVENTION

This invention generally relates to the field of endoscope. More specifically, this invention relates to a flexible digital ureteroscope, which is at least partially disposable.

BACKGROUND OF THE INVENTION

A urinary tract endoscope, such as a ureteroscope or a cystoscope, may be used for examining the inside of a urinary tract. Currently, many hospitals are still using optical-fiber-based endoscopes for urinary tract examinations. For clinical reasons, the optical fibers inside the endoscope's catheter must be thin enough so that the insertion part may pass through the unitary tract. As such, the resolution of the images captured and delivered by the optical fibers is relatively low. Furthermore, frequent angulations of the catheter may break the optical fibers inside, causing malfunctions.

Urinary tract endoscopes with digital imaging unit (e.g., digital camera) mounted on the tips of their catheters (hereinafter, "digital ureteroscopes") are becoming popular on the market. Such digital ureteroscopes often have fiber bundles on the tips and an external light source in an enclosure, which make these ureteroscopes expensive. In addition, sterilizing, reprocessing, or repairing these ureteroscopes are also costly and time consuming. And consecutive endoscopic procedures are often delayed because of reprocessing and repairs.

Thus, an inexpensive, partially disposable, and flexible digital ureteroscope that can solve the above problems is needed.

SUMMARY OF THE INVENTION

This invention provides a flexible digital ureteroscope that is at least partially disposable. The ureteroscope's insertion tip is a rigid or semi-rigid structure having a small diameter, which reduces pain or discomfort when being inserted into a patient's urinary tract. The ureteroscope provides high resolution images and videos to facilitate surgical procedures. The present invention also reduces manufacturing cost of the ureteroscope, making it possible to dispose at least the catheter part of the ureteroscope, which greatly reduces the risk of cross infection caused by incomplete sterilization.

In one embodiment, the flexible digital ureteroscope includes a single-use catheter and a handle. The single-use catheter comprises a distal end, a bend portion, and a proximal portion. The distal end of the catheter comprises a rigid or semi-rigid shell, which is manufactured, through injection molding, with a mix of polymer composite material with graphene nano-filler for enhancing thermal dissipation. The shell houses a micro illumination module and a micro camera module which has an image sensor microchip and a set of micro lenses. The catheter contains a working channel, at least one steering wire, and wire sliding groove(s). The proximal portion of the catheter is connected to the handle via a handle-catheter connector. The image sensor microchip is connected to a host interface in the handle via a plurality of conducting wires. The micro illumination module comprises one or more LED light sources. The handle is connected to a host machine via a cable, through which the host machine supplies electric power to the LED light source and the image sensor microchip and receives image data from the image sensor microchip for processing and displaying. The host machine may also transmit the image data to a computer or a mobile device through a wired or wireless communication link for further processing or convenience of displaying.

In one embodiment, the handle is a reusable handle which contains a compact battery power source, for supplying electric power to the LED light source and the image sensor microchip, and/or a wireless communication module for transmitting image data to the host machine. In this case, the handle-catheter connector can removably connect the handle with the catheter.

Compared with existing technologies, the present invention has the following advantages: The distal end of the catheter is a compact and rigid or semi-rigid structure that allows easy insertion into a patient's urinary tract; the micro lenses, the image sensor microchip, and the micro illumination module are placed inside the rigid or semi-rigid shell of the distal end in a compact and orderly arrangement, reducing the French scale of the cross-section of the tip of the distal end as much as possible to alleviate patients' pain. The rigid or semi-rigid shell of the distal end is made of a mix of polymer composite material with graphene nano-filler rather than metal. The graphene nano-filler enhances the thermal dissipation capacity of the shell. The tip of the shell is transparent so that the LED light can pass through. The catheter has different degrees of stiffness at different portions. The high-resolution image sensor microchip (e.g., a CMOS microchip) matches the size and rectangular or square shape of the micro lenses, greatly optimizing the optical effect and utilizing more pixels on the image sensor; the French scale of the image sensor microchip and the micro lenses is small than 3.82Fr, and the resolution is no less than 400×400 pixels. Multiple measures are used to reduce the manufacturing cost of the ureteroscope, including using LED light sources, plastic micro lenses, and polymer composite materials for the shell and the catheter, making it a good candidate for single use purposes. The present invention reduces the risk of cross infection and increases the image quality in ureteroscopic procedures. Steering wires are installed inside the catheter so that it can turn 0~275° towards two opposite directions.

BRIEF DESCRIPTION OF THE DRAWINGS

The subject matter, which is regarded as the invention, is particularly pointed out and distinctly claimed in the claims at the conclusion of the specification. The foregoing and other features and also the advantages of the invention will be apparent from the following detailed description taken in conjunction with the accompanying drawings.

DETAILED DESCRIPTION

Figure 1:
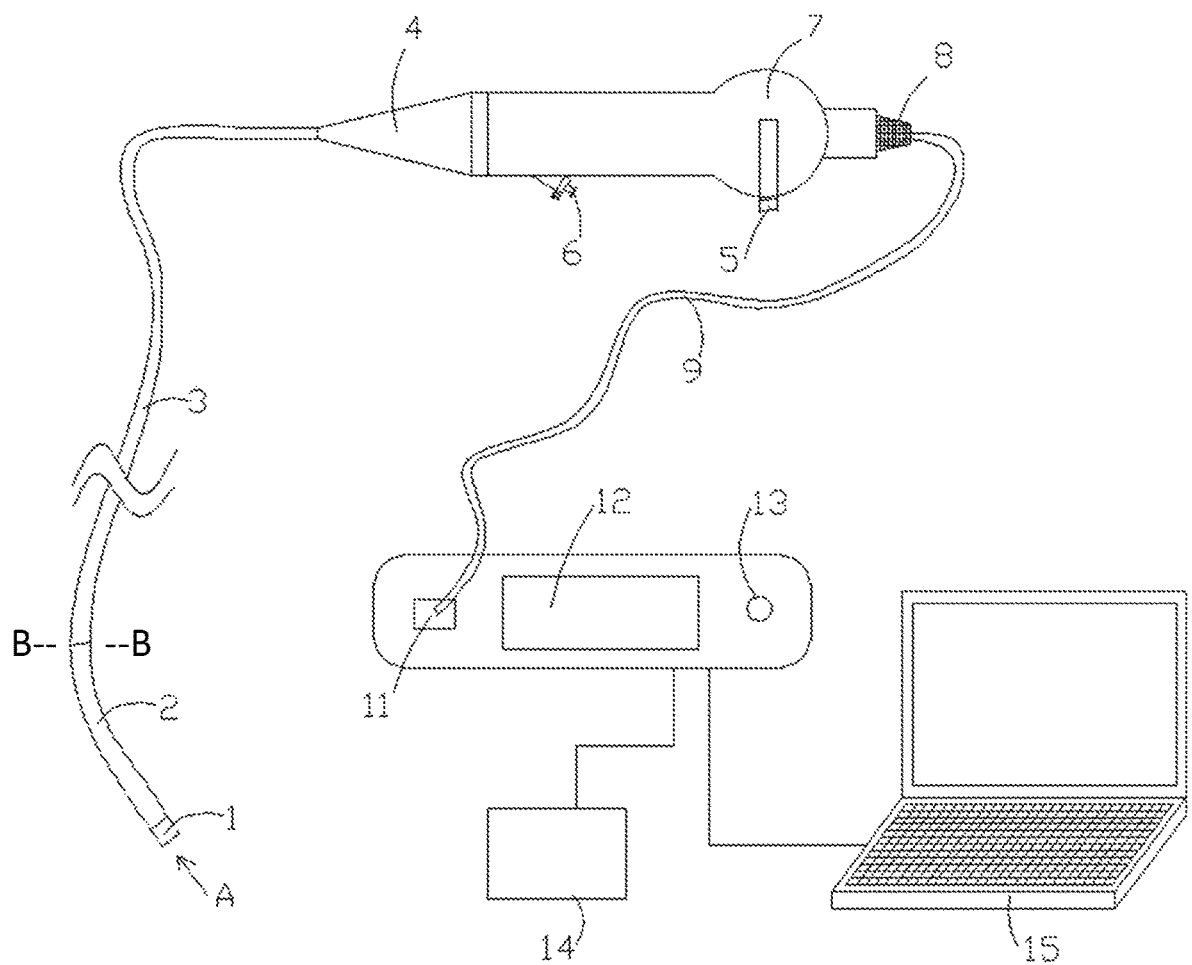
FIG. 1 illustrates a flexible digital ureteroscope as part of an endoscopic system, according to one embodiment of the present invention.

FIG. 1 illustrates an endoscopic system. In one embodiment, the endoscopic system includes a flexible digital ureteroscope, a host machine 12, and one or more external terminals 14 and 15. The ureteroscope includes a catheter and a handle 7. In one embodiment, both the catheter and the handle 7 are disposable. In this case, the catheter and the handle 7 are manufactured as an integral part, or the catheter is fixed with the handle 7 via a handle-catheter connector 4. Alternatively, only the catheter is disposable and the handle 7 may be sterilized and reused for multiple times. In this case, the catheter is removably connected to the handle 7 via a handle-catheter connector 4.

Figure 2:
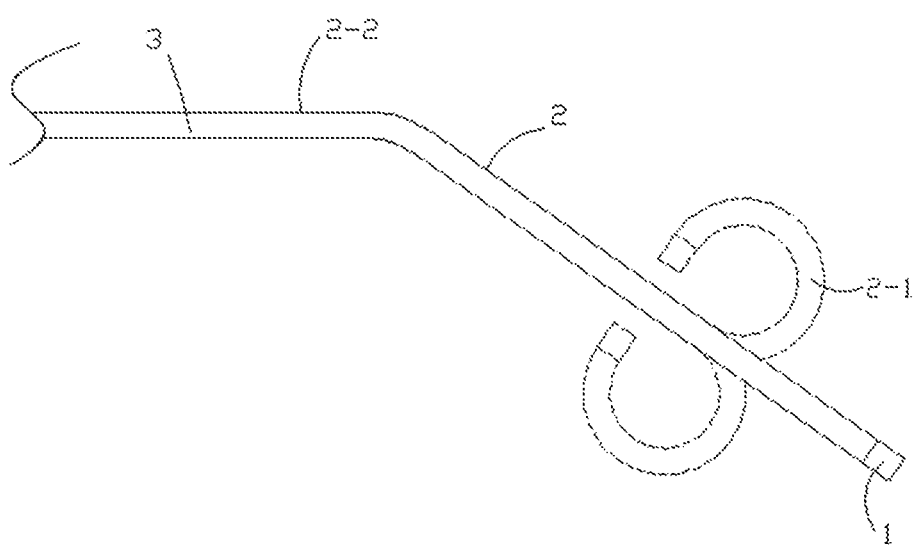
FIG. 2 illustrates the single-use catheter of the flexible digital ureteroscope shown in FIG. 1, according to one embodiment of the present invention.

In one embodiment, the catheter is a flexible catheter whose French scale is less than 9.6Fr and is preferably in the range of 7.2~9.6Fr. The catheter includes a distal end 1, a bend portion 2, and a proximal portion 3. As discussed later in detail, the distal end 1 has a rigid or semi-rigid shell that allows easy insertion of the catheter into a patient's urinary tract. The rigid or semi-rigid shell houses a micro camera module having an image sensor microchip and a set of micro lenses and a micro illumination module. The front section of a working channel runs through the distal end and the shell has an opening on the front surface which is coupled to the working channel. In one embodiment, the wall of the front section of the working channel that runs through the distal end is formed as part of the shell, which is coupled to the remaining section of the working channel. The French scale of the working channel is not less than 3.6Fr, and the inner diameter of the working channel is not less than 1.2 millimeters to allow regular surgery devices to pass through inside the body of a patient. The bend portion 2 of the catheter is made of certain flexible medical-grade polymer materials to allow for steerability of the catheter and reduce discomfort to patients. As shown in FIG. 2, the bend portion 2 includes an active bend portion 2-1 and a passive bend portion 2-2. The active bend portion 2-1 is controlled by two steering wires (e.g., steel wires) to bend in two directions, one being used for bending the active bend portion 2-1 to one direction with a 0~275° range, the other being used for bending the active bend portion 2-1 to the opposite direction with the same degree range. Other number of steering wires (e.g., 1, 3, or 4) may be implemented here as well. In contrast, the passive bend portion 2-2 bends according to the shape of urinary tract during insertion. The proximal portion 3 is made of rigid or semi-rigid polymer material to support the insertion of the distal end 1 and the bend portion 2 into the urinary tract of a patient. Alternatively, the bend portion 2 and the proximal portion 3 are made as an integral part with the same type of polymer material through an extrusion process, but additional supporting structures (e.g., metal, hard plastic) can be added in the proximal portion to increase mechanical performances. Yet in another embodiment, the catheter, or part of it, has at least three superposed layers of materials, including an outer layer, a middle layer, and an inner layer, secured together. The outer layer and the inner layer are made of a same polymer composite material or two different polymer composite materials as an integral part by an extrusion process, and the middle layer comprises a braided metal layer which enhances torque ability and Kink characteristics of the multi-layer catheter.

The handle 7 includes a working channel port 6, a steering controller 5, and a handle-catheter connector 4. The proximal portion 3 is connected to the handle 7 via the handle-catheter connector 4. As discussed above, the connection may be a fixed connection, in which case the handle and the catheter as a whole is disposed after an operation, or a removable connection, in which case a used catheter is disconnected from the handle and disposed and a new catheter is connected to the handle for the next endoscopic procedure. The working channel port 6 engages with various surgical instruments and irrigation devices, as needed, for operations such as stone breaking and retrieval, etc. The steering controller 5 controls the one or more steering wires that are connected to the active bend portion 2-1 to deflect the distal end 1 to the desired location.

In one embodiment, the handle 7 also includes a host interface 8 for communicating with and receiving electric power from the host machine 12 via a cable 9. The host interface 8 transmits image data captured at the distal end 1 to the host machine 12 for processing, storing, and displaying. Alternatively, the host interface 8 is a wireless interface that can wirelessly transmit image data to the host machine 12. The wireless interface may implement various protocols, including but not limited to Wi-Fi, Bluetooth, ZigBee, Z-Wave, etc. The handle 7 may further include a compact battery module for supplying power to the micro camera module and the micro illumination module of the distal end 1 and the host interface 8 of the handle 7. In one embodiment, the handle 7 includes a LED light source which provides illumination to the distal end via one or more sets of optical fibers.

In one embodiment, the host machine 12 includes a microprocessor and a display for processing and displaying the image data received from the ureteroscope. The host machine 12 may also be connected to one or more personal computers or mobile devices 14 and 15 for further processing and displaying the image data.

Figure 3:
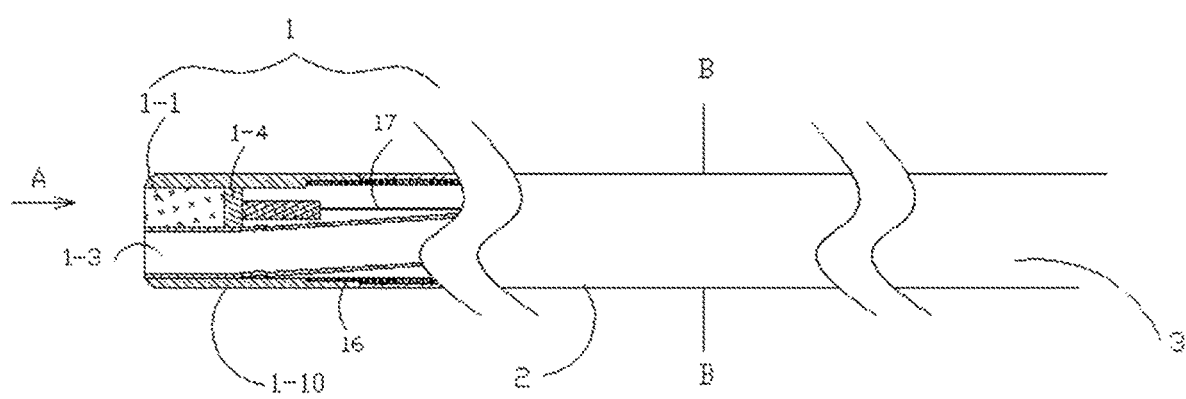
FIG. 3 is a sectional view of the catheter's distal end shown in FIG. 2, according to one embodiment of the present invention.

FIG. 3 is a sectional view of the catheter's distal end shown in FIG. 2. As shown, the catheter's distal end 1 comprises a shell 1-10, which is manufactured (through injection modeling, for example) with a mix of polymer composite material with graphene nano-filler for enhancing thermal dissipation. The polymer composite material with graphene nano-filler can be made by a melt mixing process or a powder mixing process. In the powder mixing process, the polymer powder and the graphene nano-filler powder are mixed so that the graphene nano-filler powder particles are evenly attached to the surface of the polymer powder particles. Then the mixed material is formed into the structure of the shell via a heat-and-press process. The polymer may be any kind of plastic, resin (natural or synthetic), or synthetic fiber that is suitable for medical uses. The shell houses a micro camera module having an image sensor microchip 1-4 and a set of micro lenses 1-1. During an endoscopic procedure, the micro camera module captures images of the tissue area or organ being examined and transmits the image data to the handle 7 and then to the host machine 12 for visual display. Specifically, the image sensor microchip 1-4 is connected to a plurality of conducting wires 17 for receiving electric power from and sending image data to the handle 7. In one embodiment, the whole conducting wire bundle 17 has a diameter less than 0.6 millimeter. The shell 1-10 further houses a micro illumination module that comprises two LED light sources 1-2 (shown in FIGS. 4 and 5) or two sets of optical fibers 18 (shown in FIG. 7), the front part of a working channel 1-3, and two steering wires 16 (shown in FIGS. 6 and 7). The set of micro lenses 1-1, the image sensor microchip 1-4, the LED light sources 1-2, and the plurality of conductive wires are bundled together and are bonded with the inner walls of the shell with adhesives, such as epoxy resin adhesive, AB adhesive, or UV-curable adhesive. To enhance thermal dissipation, the adhesives are mixed with graphene nano-filler as well.

Figure 4:
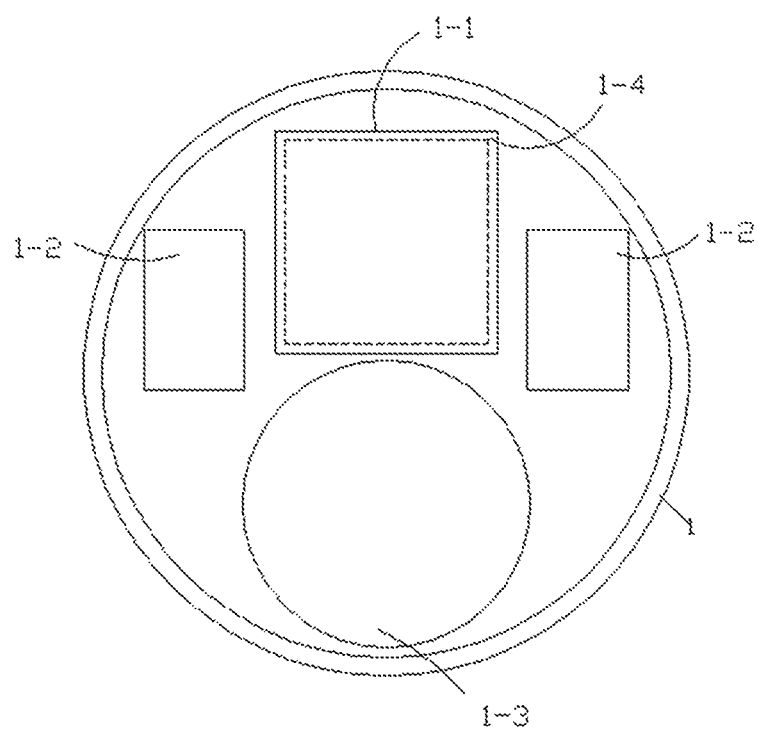
FIG. 4 is a sectional view of the distal end of the catheter along direction A shown in FIG. 3, according to one embodiment of the present invention.
Figure 5:
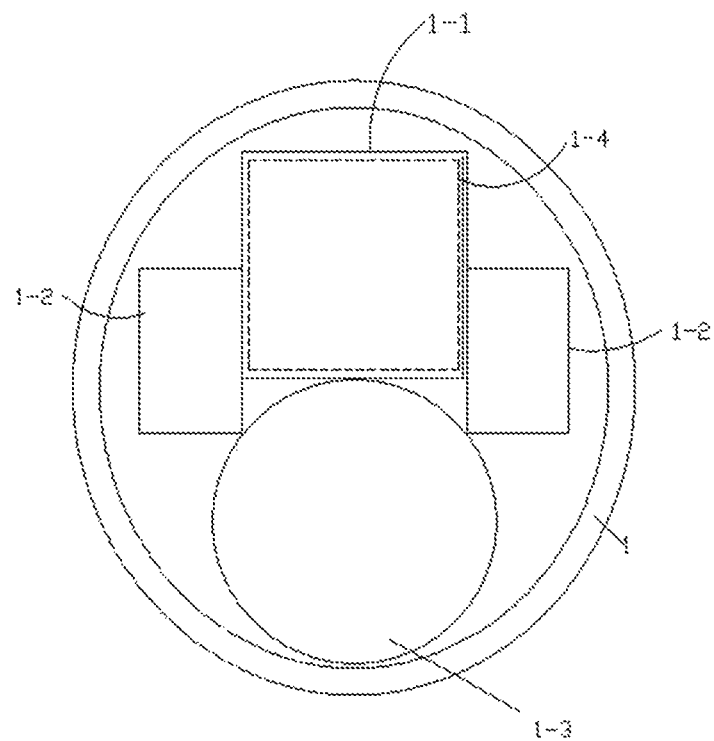
FIG. 5 is a sectional view of the distal end of the catheter along direction A shown in FIG. 3, according to one embodiment of the present invention.

FIG. 4 is a sectional view of the distal end of the catheter along direction A shown in FIG. 3. As shown, the distal end 1 has a circular cross-section. The set of micro lenses 1-1 has a rectangular or square shape. Behind the micro lenses is the image sensor microchip 1-4. The working channel 1-3 is arranged next to the micro lenses 1-1. There are two LED light sources 1-2, one on each side of the micro lenses 1-1. Alternatively, the distal end 1 has an oval cross-section as shown in FIG. 5. It should be noted that these are just examples of how the LED light sources, the micro lenses, and the working channel may be arranged inside the shell 1-10 of the distal end 1. In addition, the number of the LED light sources, micro lenses, as well as working channel may also change depending on the particular application and design.

Figure 6A:
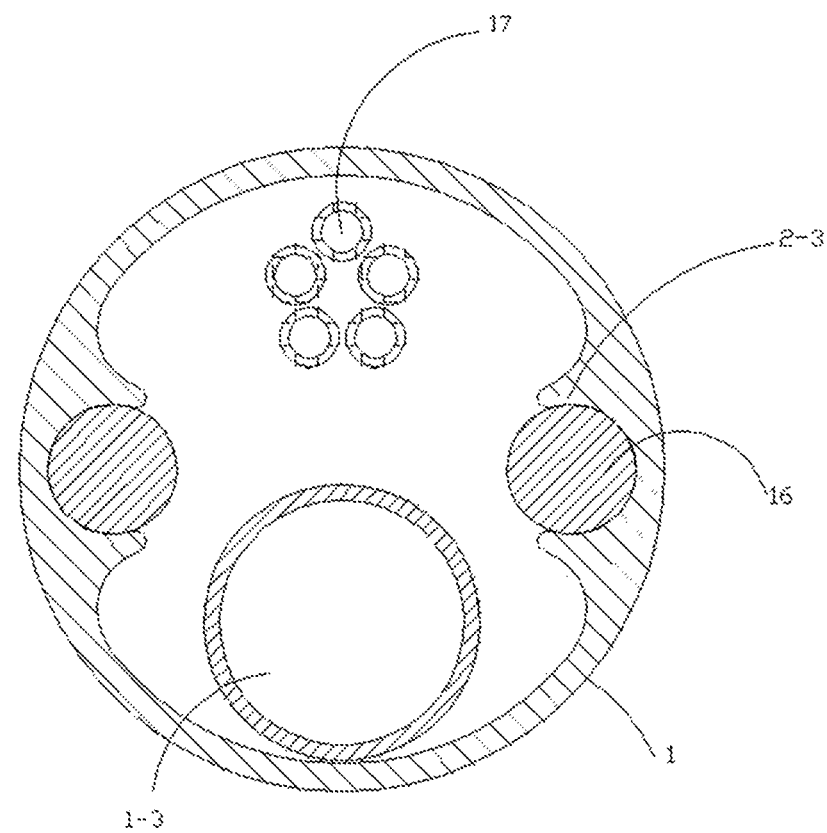
FIG. 6A is a cross-sectional view of B-B shown in FIG. 1, according to one embodiment of the present invention.

FIG. 6A is a cross-sectional view of B-B shown in FIG. 1. This is a cross-sectional view of the bend portion 2 of the catheter. As shown, there are a plurality of conducting wires 17 extending along the catheter to connect the image sensor microchip 1-4 and the LED light sources 1-2 to the handle 7. Certain conducting wires 17 transmit image data from the image sensor microchip 1-4 to the host interface 8 of the handle 7 and other conducting wires 17 transmit electric power from the handle 7 to the image sensor microchip 1-4 and the LED light sources 1-2. Also, there are two steering wires 16 extending along the catheter, one on each side and within a wire sliding groove 2-3, respectively. The wire sliding grooves 2-3 are formed as part of the inner wall of the catheter and each wire sliding groove 2-3 holds a steering wire 16 in place so that when a surgeon turns the steering controller 5 on the handle 7 in one direction, one of the steering wire 16 would slide within the corresponding wire sliding groove 2-3 and pull the active bend portion 2-1 to bend towards one direction. And if the surgeon turns the steering controller 5 in the opposite direction, the other steering wire 16 would pull the active bend portion 2-1 to bend towards the opposite direction. The degree of the bend is determined by the extent of the surgeon's turn of the steering controller.

Figure 6B:
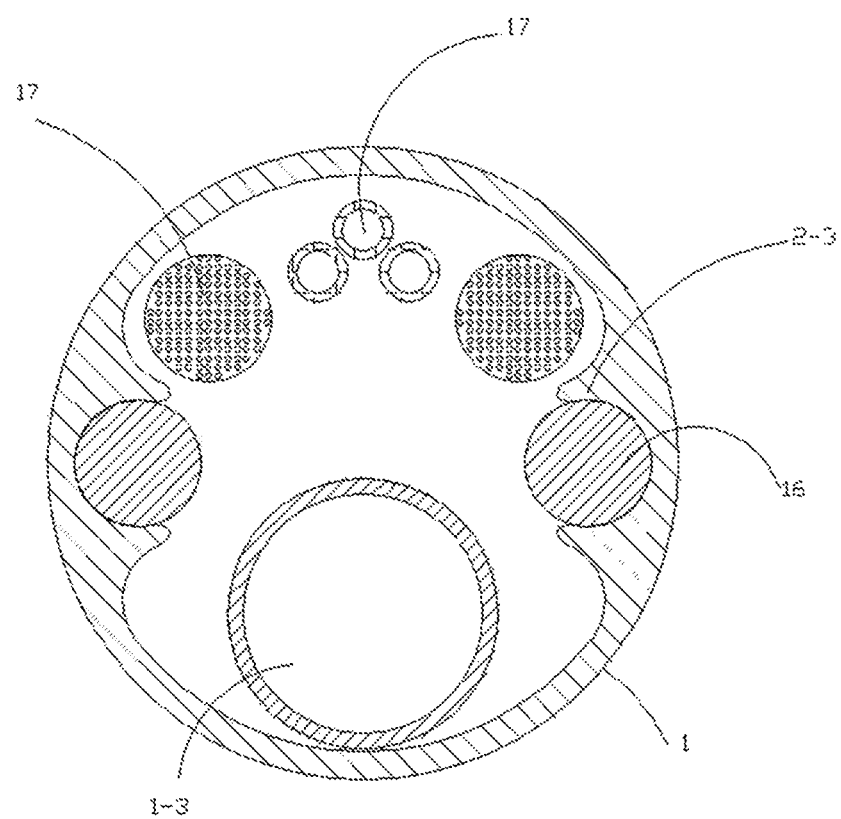
FIG. 6B is a cross-sectional view of B-B shown in FIG. 1, according to one embodiment of the present invention, where the LED light sources are installed inside the handle.

FIG. 6B is a cross-sectional view of B-B shown in FIG. 1, according to one embodiment of the present invention where the LED light sources are installed inside the handle. Because the LED light sources are installed inside the handle 7, two conducting wires 17, which are needed for transmitting electric power to the LED light sources in the embodiment shown in FIG. 6A, are not needed. Instead, two sets of optical fiber bundles 18 are installed to transmit light from the LED light sources located inside the handle 7 to the distal end 1.

In the embodiments shown in FIGS. 6A and 6B, the bend portion and the proximal portion of the catheter are formed as an outer tube and the working channel is an inner tube enclosed inside the outer tube. In one embodiment, the working channel 1-3 is attached to the inner wall of the catheter by glues, for example, so that it doesn't wiggle inside the catheter, therefore not interfering with the conducting wires 17 and/or the optical fibers 18. However, to reduce cost, the working channel 1-3 is only attached at both ends of the catheter. In one embodiment, the French scale of the working channel 1-3 is not less than 3.6Fr, and the inner diameter of the working channel 1-3 is not less than 1.2 millimeter to allow regular surgery devices to pass through inside the body of a patient.

Figure 7:
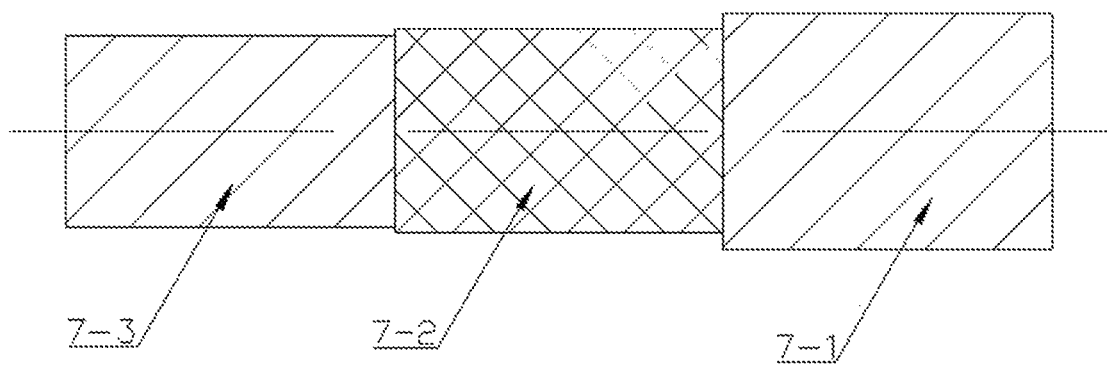
FIG. 7 illustrates an embodiment of the outer tube of a catheter that has at least three superposed layers of materials.

In the embodiments shown in FIGS. 6A and 6B, the outer tube of the catheter has at least three superposed layers of materials, including an outer layer, a middle layer, and an inner layer, secured together. FIG. 7 illustrates such an example. As shown, the outer layer 7-1 and the inner layer 7-3 are made of the same polymer composite material or two different polymer composite materials as an integral part by an extrusion process, and the middle layer 7-2 comprises a braided metal layer which enhances torque ability and Kink characteristics of the multi-layer catheter.

Figure 8:
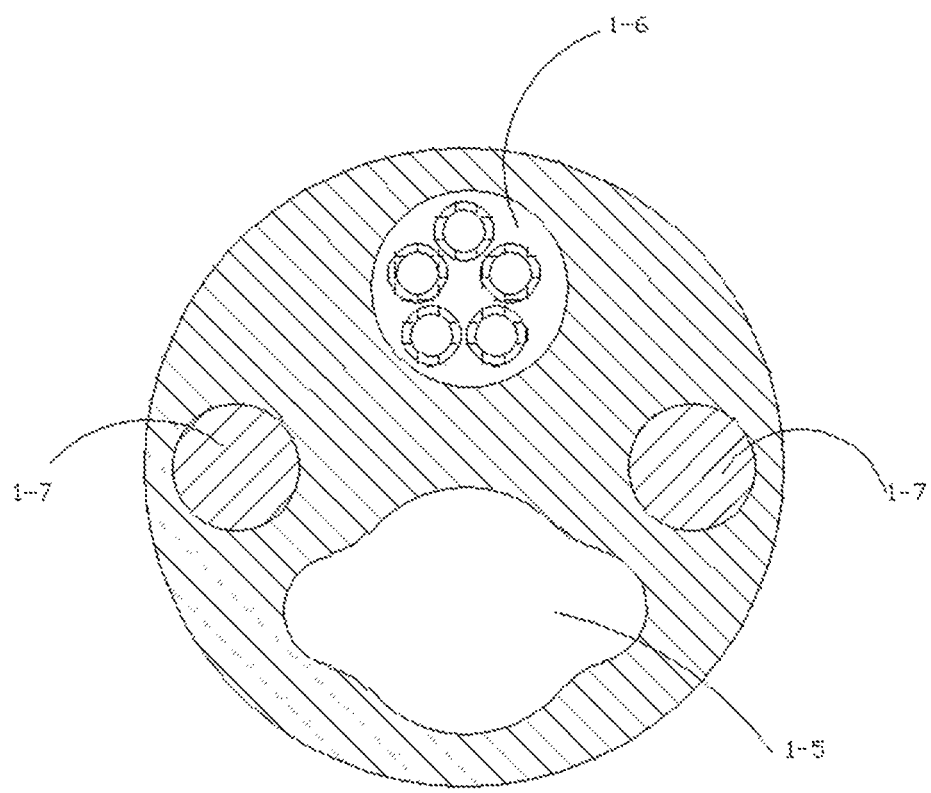
FIG. 8 is a cross-sectional view of B-B shown in FIG. 1, according to one embodiment of the present invention.

FIG. 8 is a cross-sectional view of B-B of a different embodiment of the catheter, whose bend portion and proximal portion are formed as a multi-channel tube. As shown, the catheter has a channel 1-5 acting as a working channel, a channel 1-6 for housing the plurality of conducting wires 17, and two channels 1-7 for installing the steering wires 16, respectively. In this embodiment, the bend portion, the proximal portion, and the various channels described above are formed as an integral part with polymer material by an extrusion process.

Figure 9:
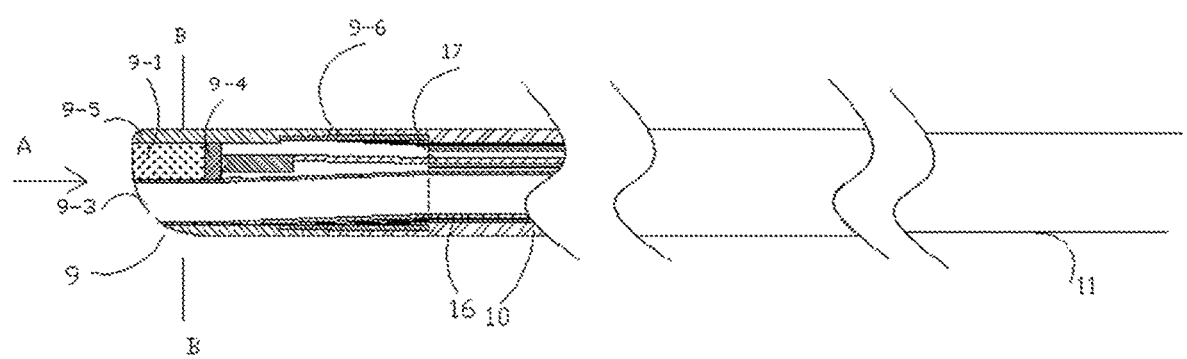
FIG. 9 is a sectional view of the catheter shown in FIG. 2, according to one embodiment of the present invention.
Figure 10:
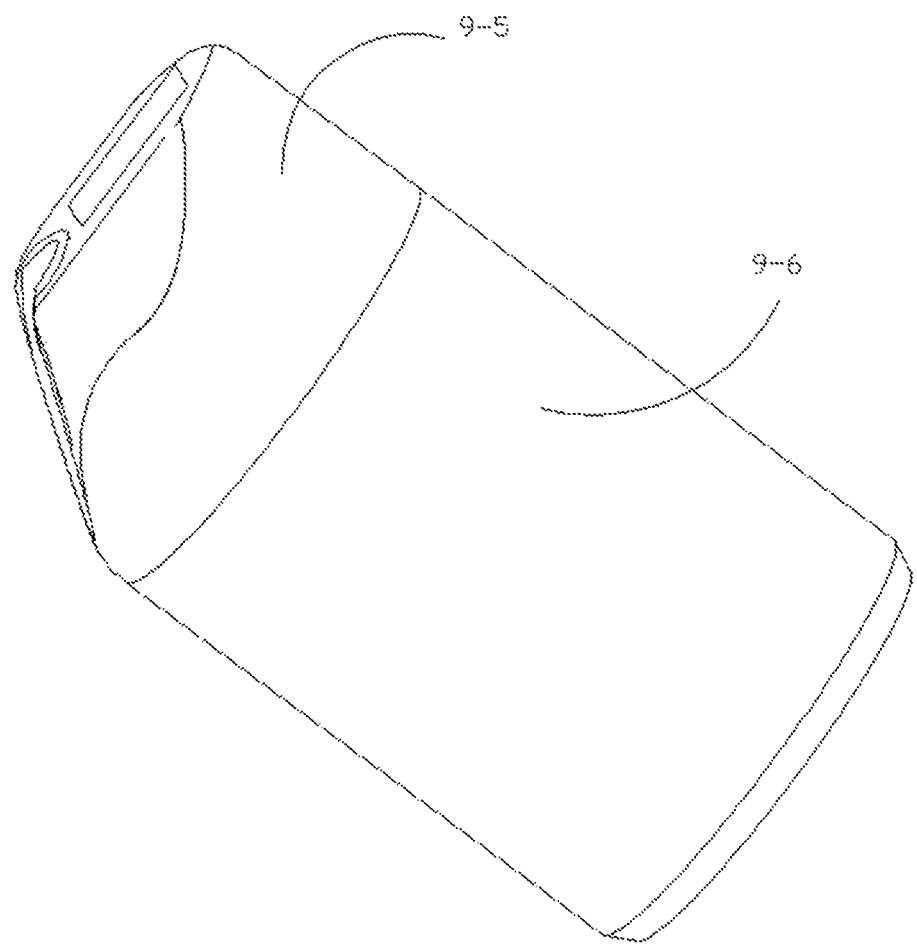
FIG. 10 is a perspective view of the distal end of the catheter shown in FIG. 2.
Figure 11:
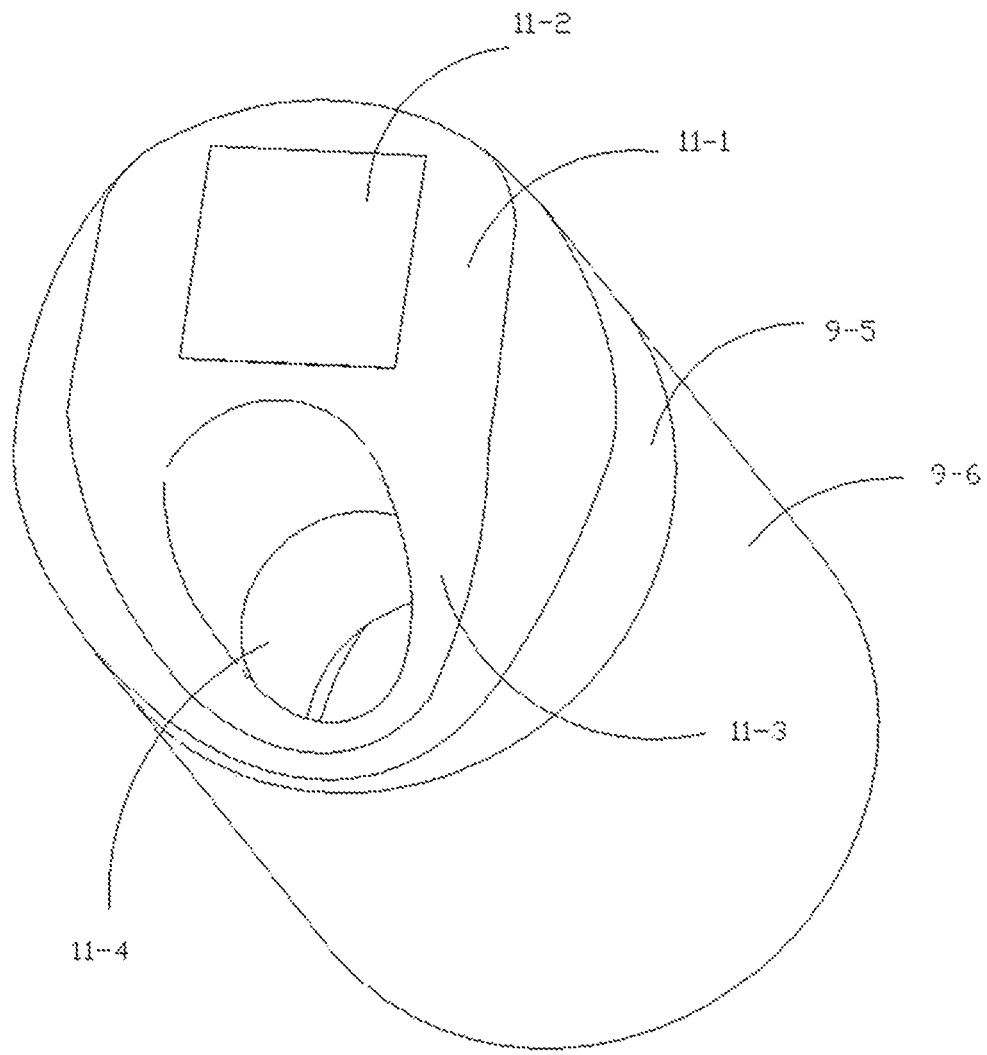
FIG. 11 is another perspective view of the distal end of the catheter shown in FIG. 2.

FIG. 9 is a sectional view of a different embodiment of the catheter shown in FIG. 1. Similarly, this embodiment of the catheter also has a distal end 9, a bend portion 10, and a proximal portion 11. Referring to FIGS. 10 and 11, the distal end 1 has a tip 9-5 and a tube fitting 9-6. The tip 9-5 has a flat front surface 11-1, beneath which is a chamber 11-2 for housing a set of micro lenses 9-1 and an image sensor microchip 9-4. The tip 9-5 has a slopped side surface 11-3, beneath which is a chamber 11-4 for functioning as the opening of a working channel 1-3. Both the font surface 11-1 and the side surface 11-3 have rounded corners and the tip 9-5 have a tapered shape overall to reduce the difficulty of insertion of the catheter into a patient's body and therefore reducing discomfort to the patient. The distal end 9 is coupled to the bend portion 10 via a tube fitting 9-6. As shown, the distal end 9 is fitted onto one end of the tube fitting 9-6 by tightly wrapping around the entire outer surface of the end. Glues or other sealing material may be used to strengthen the connection and seal any small gaps. Similarly, the bend portion 10 is tightly fitted onto the other end of the tube fitting 9-6. In one embodiment, the tube fitting 9-6 is made of stainless steel or ceramic and is attached to one or more steering wires 16 by welding or gluing. The other ends of the steering wire or wires 16 are attached to the steering controller 6 on the handle 7. The steering controller 6 controls the steering wire or wires 16 to bend the active bend portion 2-1 of the catheter in one or more directions.

Figure 12:
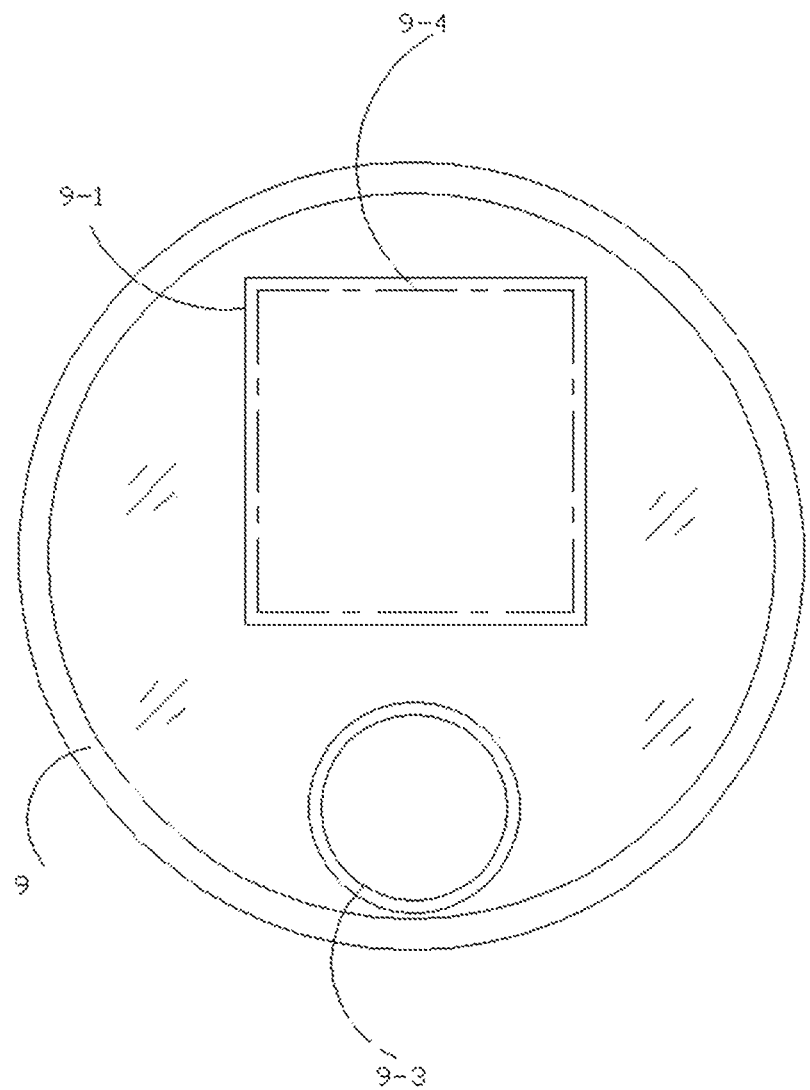
FIG. 12 is a sectional view of the catheter along direction A shown in FIG. 9, according to one embodiment of the present invention.
Figure 13:
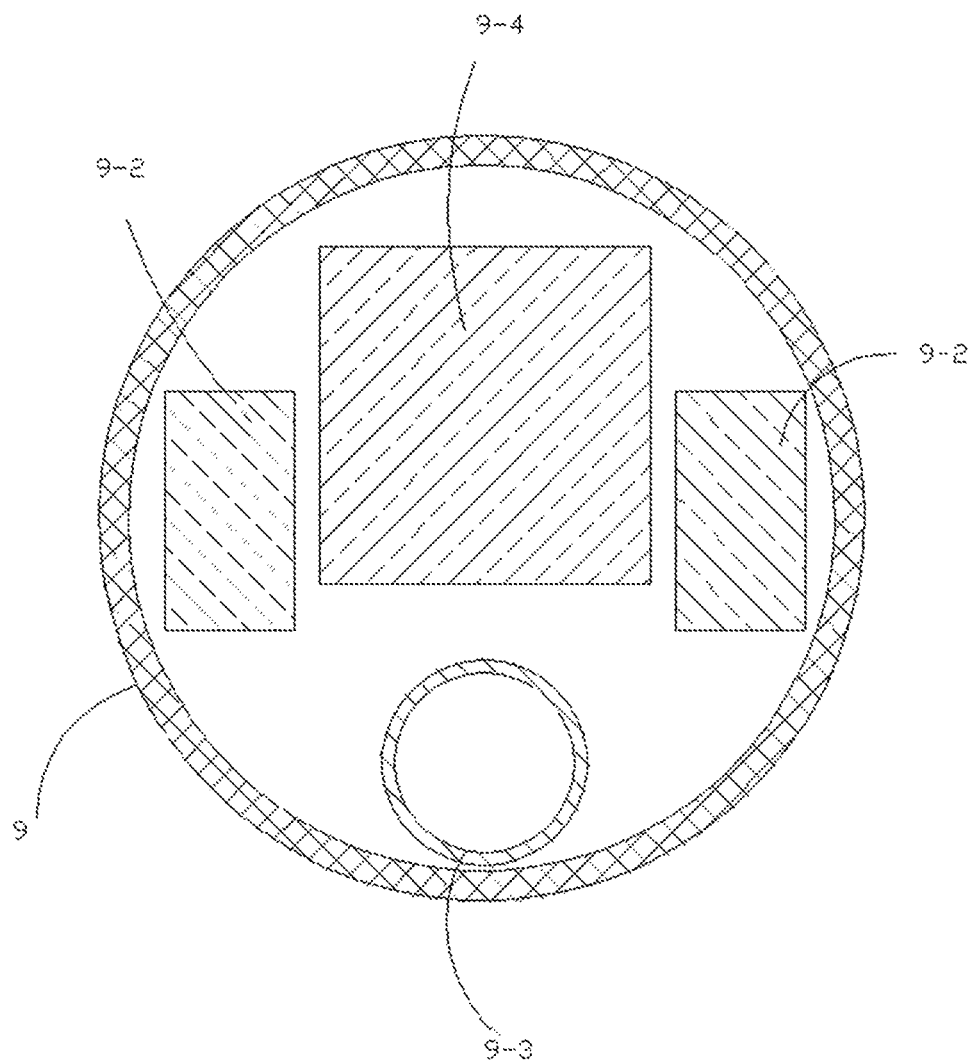
FIG. 13 is a cross-sectional view of B-B shown in FIG. 9, according to one embodiment of the present invention.

FIG. 12 is a front view of the distal end along direction A shown in FIG. 9, and FIG. 13 is a cross-sectional view of B-B shown in FIG. 9. As shown, the tip 9-5 of the distal end 9 is transparent and made of a mix of polymer composite material with graphene nano-filler for enhancing thermal dissipation. The opening for the working channel 9-3 has an internal diameter not less than 1.2 millimeters, and its French scale is not less than 3.6Fr. The tip 9-5 houses the set of micro lenses 9-1 which is square-shaped with a size of 1 millimeter by 1 millimeter. Right behind the micro lenses 9-1 is the image sensor microchip 9-4, whose French scale is 3.82Fr or less and resolution is 0.16 million pixels. The micro lenses 9-1 and the image sensor microchip 9-4 are designed to have the same size and shape to best utilize the 0.16 million pixels while minimizing the French scale of the distal end 9. The tip 9-5 also houses two LED light sources 9-2.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments. Furthermore, it is intended that the appended claims cover any and all such applications, modifications, and embodiments within the scope of the present invention.

We claim:

1. A flexible digital ureteroscope comprising
a catheter, intended for a single use, wherein the catheter comprises
   i. a proximal portion coupled to a handle;
   ii. a bending portion; and
   iii. a distal end comprising
      a. a cross-section area having its circumference with a French scale between 7.2 and 9.6 Fr;
      b. a transparent taper/bullet shaped shell (TTBSS) comprising a mix of polymer composite material(s) and graphene nano-filler material(s), wherein the TTBSS comprises a taper shaped slop side and an opening in a central area of the taper shaped slop side, wherein the opening serves as a terminal of a working channel inside and along the flexible digital ureteroscope throughout the catheter by going through its proximal portion, bending portion, and distal end;
      c. at least one CMOS image sensor microchip having a resolution not less than 0.16 million pixels, housed inside the TTBSS;
      d. a set of squared-shaped micro lenses, each having a size not larger than 1.0 millimeter by 1.0 millimeter, stacked one by one from a surface of the CMOS image sensor microchip, housed inside the TTBSS, wherein a farthest lens of the set of squared-shaped micro lenses away from the CMOS image sensor microchip serves as a part of the TTBSS, wherein this part of TTBS does not comprise any graphene and is located at a distal terminal of the distal end;
      e. at least one LED light source positioned for illuminating only an object outside of the TPBSS by positioning the LED light source(s) behind the CMOS image sensor microchip(s) for minimizing light contamination towards any/all image sensing surface(s) of the image sensor microchip(s) inside the TTBSS;
      f. a plurality of metal wires for transmitting image data and electric power, partially housed inside the transparent shell and partially located throughout a rest of the catheter; and
      g. an adhesive for bonding the above components inside the TTBSS together, wherein the adhesive comprises a mix of polymer composite material(s) and graphene nano-filler material(s).

2. The flexible digital ureteroscope of claim 1, wherein the farthest lens of the set of squared-shaped micro lenses away from the CMOS image sensor microchip is a part of the TTBSS is located at a distal tip of the TTBSS.

3. The flexible digital ureteroscope of claim 2, wherein the polymer composite material comprises one of plastic material, resin material, synthetic fiber material, and adhesive material and is manufactured by melt mixing or powder mixing.

4. The flexible digital ureteroscope of claim 1, where the catheter has at least three superposed layers of materials, including an outer layer, a middle layer, and an inner layer, secured together, and wherein the outer layer and the inner layer are made of a same polymer composite material or two different polymer composite materials as an integral part by an extrusion process, and the middle layer comprises a braided metal layer.

5. The flexible digital ureteroscope of claim 4, wherein the extrusion process forms a single channel extending along the entire integral part.

6. The flexible digital ureteroscope of claim 4, wherein the extrusion process forms a first channel extending along the entire integral part for housing a plurality of conducting wires, a second channel extending along the entire integral part for housing two steering wires, and a third channel extending along the entire integral part to function as the working channel.

7. The flexible digital ureteroscope of claim 1, wherein the proximal portion and the bend portion of the catheter are made of different polymer composite materials and braided metal tubes as an integral part by an extrusion process and the two portions have different hardness and flexibility.

8. The flexible digital ureteroscope of claim 1 further comprises a tube fitting through which the distal end is coupled to the bend portion, wherein the tube fitting is made of stainless steel or ceramic and at least one steering wire is fixed onto the tube fitting.

9. The flexible digital ureteroscope of claim 1, wherein the handle comprises a steering controller, a handle-catheter connector that couples the handle to the catheter, and a host interface that connects the handle to a host machine.

10. A flexible digital ureteroscope comprising a catheter, intended for a single use, wherein the catheter comprises
   iv. a proximal portion coupled to a handle;
   v. a bending portion; and
   vi. a distal end comprising
      h. a cross-section area having its circumference with a French scale between 7.2 and 9.6 Fr;
      i. a transparent taper/bullet shaped shell (TTBSS) comprising a mix of polymer composite material(s) and graphene nano-filler material(s), wherein the TTBSS comprises a taper shaped slop side and an opening in a central area of the taper shaped slop side, wherein the opening serves as a terminal of a working channel inside and along the flexible digital ureteroscope throughout the catheter by going through its proximal portion, bending portion, and distal end;

j. at least one CMOS image sensor microchip having a resolution not less than 0.16 million pixels, housed inside the TTBSS;

k. a set of squared-shaped micro lenses, each having a size not larger than 1.0 millimeter by 1.0 millimeter, stacked one by one from a surface of the CMOS image sensor microchip, housed inside the TTBSS, wherein a farthest lens of the set of squared-shaped micro lenses away from the CMOS image sensor microchip serves as a part of the TTBSS, wherein this part of TTBS does not comprise any graphene and is located at a distal terminal of the distal end;

l. at least one LED light source positioned for illuminating only an object outside of the TPBSS by positioning the LED light source(s) behind the CMOS image sensor microchip(s) for minimizing light contamination towards any/all image sensing surface(s) of the image sensor microchip(s) inside the TTBSS;

m. a plurality of metal wires for transmitting image data and electric power, partially housed inside the transparent shell and partially located throughout a rest of the catheter; and n. an adhesive for bonding the above components inside the TTBSS together, wherein the adhesive comprises a mix of polymer composite material(s) and graphene nano-filler material(s).

11. The distal end of claim 10, wherein the polymer composite material comprises one of plastic material, resin material, and synthetic fiber material.

* * * * *